US007812010B2

(12) United States Patent
DiPiano et al.

(10) Patent No.: US 7,812,010 B2
(45) Date of Patent: Oct. 12, 2010

(54) PHARMACEUTICAL PREPARATIONS FOR TREATMENTS OF DISEASES AND DISORDERS OF THE BREAST

(75) Inventors: Gerianne T. DiPiano, Malvern, PA (US); Peter Kevin Mays, Philadelphia, PA (US); John Ziemniak, Gwynedd Valley, PA (US)

(73) Assignee: Femmepharma, Inc., Wayne, PA (US)

( * ) Notice: Subject to any disclaimer, the term of this patent is extended or adjusted under 35 U.S.C. 154(b) by 722 days.

(21) Appl. No.: 10/751,056

(22) Filed: Jan. 2, 2004

(65) Prior Publication Data

US 2004/0229813 A1 Nov. 18, 2004

Related U.S. Application Data

(60) Provisional application No. 60/437,778, filed on Jan. 2, 2003.

(51) Int. Cl.
A61K 31/56 (2006.01)
A61K 9/00 (2006.01)
A61K 9/14 (2006.01)

(52) U.S. Cl. ............... 514/171; 514/169; 424/401; 424/400; 424/484

(58) Field of Classification Search ........... 514/899, 514/169, 171; 424/430, 484, 400, 401
See application file for complete search history.

(56) References Cited

U.S. PATENT DOCUMENTS

| | | | |
|---|---|---|---|
| 3,921,636 A | 11/1975 | Zaffaroni | |
| 3,927,216 A | 12/1975 | Witkowski et al. | |
| 4,081,533 A | 3/1978 | Cheesman | |
| 4,107,288 A | 8/1978 | Oppenheim et al. | |
| 4,272,398 A | 6/1981 | Jaffe | |
| 4,286,587 A | 9/1981 | Wong | |
| 4,291,028 A | 9/1981 | Vorys | |
| 4,292,315 A | 9/1981 | Vorys | |
| 4,391,797 A | 7/1983 | Folkman et al. | |
| 4,524,359 A | 6/1985 | Champagne | |
| 4,525,340 A | 6/1985 | Lange et al. | |
| 4,588,724 A | 5/1986 | Greenway, III et al. | |
| 4,591,496 A | 5/1986 | Cohen et al. | |
| 4,673,405 A | 6/1987 | Guittard et al. | |
| 4,756,907 A | 7/1988 | Beck et al. | |
| 4,762,717 A | 8/1988 | Crowly, Jr. | |
| 4,826,830 A | 5/1989 | Han et al. | |
| 4,861,627 A | 8/1989 | Mathiowitz et al. | |
| 4,873,092 A | 10/1989 | Azuma et al. | |
| 4,919,937 A * | 4/1990 | Mauvais-Jarvis et al. | .... 424/449 |
| 4,919,939 A | 4/1990 | Baker | |
| 4,965,128 A | 10/1990 | Greidanus et al. | |
| 4,997,653 A | 3/1991 | Igarashi et al. | |
| 5,057,317 A | 10/1991 | Iida | |
| 5,066,495 A | 11/1991 | Moro et al. | |
| 5,091,185 A | 2/1992 | Castillo et al. | |
| 5,130,137 A | 7/1992 | Crowley, Jr. | |
| 5,145,684 A | 9/1992 | Liversidge et al. | |
| 5,156,851 A | 10/1992 | Castillo et al. | |
| 5,194,259 A | 3/1993 | Soudant et al. | |
| 5,324,522 A | 6/1994 | Krenning et al. | |
| 5,330,768 A | 7/1994 | Park et al. | |
| 5,340,585 A | 8/1994 | Pike et al. | |
| 5,359,030 A | 10/1994 | Ekwuribe | |
| 5,362,720 A | 11/1994 | Labrie | |
| 5,413,797 A | 5/1995 | Khan et al. | |
| 5,417,982 A | 5/1995 | Modi | |
| 5,434,146 A | 7/1995 | Labrie | |
| 5,438,040 A | 8/1995 | Ekwuribe | |
| 5,472,704 A | 12/1995 | Santus et al. | |
| 5,482,925 A | 1/1996 | Hutsell | |
| 5,482,927 A | 1/1996 | Maniar et al. | |
| 5,494,047 A | 2/1996 | Van Os | |
| 5,510,118 A | 4/1996 | Bosch et al. | |
| 5,536,499 A | 7/1996 | Znaiden et al. | |

(Continued)

FOREIGN PATENT DOCUMENTS

DE    100 54 294    5/2002

(Continued)

OTHER PUBLICATIONS

Chan et al. Breast pain: What to do? The Hong Kong Practitioner vol. 21, Dec. 1999, p. 573-578.*

(Continued)

*Primary Examiner*—Jennifer M Kim
(74) *Attorney, Agent, or Firm*—Pabst Patent Group LLP

(57) ABSTRACT

Formulations for topical or local administration of drugs directly to the breast or chest to produce a regional or local effect with lower systemic drug levels than when an effective amount is administered systemically are disclosed herein. In a preferred embodiment, the drug is administered to the surface of the breast, areola, or directly to the nipple. The formulations provide increased patient comfort, increased bioavailability and relatively high blood levels in the region to be treated with a reduction of side effects compared to those administered systemically. The preferred formulations contain drugs in the form of micro or nanoparticles, which may be formed of drug alone or in combination with an excipient or carrier. The excipient or carrier may modify the release rates or enhance absorption into the affected area. The drug formulation may be in the form of a cream, lotion or foam.

4 Claims, 1 Drawing Sheet

U.S. PATENT DOCUMENTS

| | | | |
|---|---|---|---|
| 5,552,160 A | 9/1996 | Liversidge et al. | |
| 5,580,857 A * | 12/1996 | Oden | 514/25 |
| 5,614,212 A * | 3/1997 | D'Angelo et al. | 424/449 |
| 5,633,011 A | 5/1997 | Dong et al. | |
| 5,643,604 A | 7/1997 | Angeles Uribe et al. | |
| 5,651,976 A | 7/1997 | Price et al. | |
| 5,705,170 A | 1/1998 | Kong et al. | |
| 5,778,894 A | 7/1998 | Dorogi et al. | |
| 5,789,442 A | 8/1998 | Garfield et al. | |
| 5,843,509 A | 12/1998 | Calvo Salve et al. | |
| 5,945,109 A | 8/1999 | Schmidt et al. | |
| 5,993,856 A * | 11/1999 | Ragavan et al. | 424/489 |
| 6,071,526 A | 6/2000 | Schmidt et al. | |
| 6,087,351 A | 7/2000 | Nyce | |
| 6,358,539 B1 | 3/2002 | Murad | |
| 6,416,778 B1 * | 7/2002 | Ragavan et al. | 424/430 |
| 6,436,428 B1 | 8/2002 | Mahashabde et al. | |
| 6,482,448 B2 | 11/2002 | Tabor | |
| 6,517,864 B1 | 2/2003 | Orup Jacobsen et al. | |
| 6,652,874 B2 * | 11/2003 | Ragavan et al. | 424/430 |
| 6,743,441 B2 | 6/2004 | Sanders et al. | |
| 6,908,623 B2 | 6/2005 | Deaver et al. | |
| 2002/0150605 A1 | 10/2002 | Yui et al. | |
| 2003/0109507 A1 | 6/2003 | Franke et al. | |
| 2003/0143278 A1 | 7/2003 | DiPiano et al. | |
| 2003/0153585 A1 * | 8/2003 | Schreder et al. | 514/260.1 |
| 2003/0175329 A1 | 9/2003 | Azarnoff et al. | |
| 2004/0002503 A1 | 1/2004 | Chang et al. | |
| 2004/0018991 A1 | 1/2004 | Schmidt et al. | |
| 2004/0138314 A1 | 7/2004 | Bua | |
| 2005/0101579 A1 | 5/2005 | Shippen | |
| 2008/0153789 A1 | 6/2008 | Dmowski et al. | |
| 2008/0299207 A1 | 12/2008 | Martin | |

FOREIGN PATENT DOCUMENTS

| | | |
|---|---|---|
| EP | 0 501 056 | 9/1992 |
| EP | 0 566 135 | 10/1993 |
| GB | 767 824 | 2/1957 |
| JP | 61-500914 | 5/1986 |
| WO | WO 91/12007 | 8/1991 |
| WO | WO 95/07071 | 3/1995 |
| WO | WO 95/31973 | 11/1995 |
| WO | WO 95/31974 | 11/1995 |
| WO | WO 96/00567 | 1/1996 |
| WO | WO 96/25150 | 8/1996 |
| WO | WO 96/37232 | 11/1996 |
| WO | WO 97/29735 * | 8/1997 |
| WO | WO 98/11888 | 3/1998 |
| WO | WO 98/32422 | 7/1998 |
| WO | WO 99/24041 | 5/1999 |
| WO | WO 00/27372 | 5/2000 |
| WO | WO00/72883 A2 * | 12/2000 |
| WO | WO 02/17926 | 3/2002 |
| WO | WO 03/039553 | 5/2003 |

OTHER PUBLICATIONS

Fentiman, et al., "Dosage and duration of tamoxifen treatment for mastalgia: a controlled trial," *Br J Surg*, 75(9): 845-846 (1988).

Fentiman, et al., "Studies of tamoxifen in women with mastalgia." *Br: J. Clinical Prac. Sympt.* 68: 34-36 (1989).

Hinton, et al., "A double-blind controlled trial of danazol and bromocriptine in the management of severe cyclical breast pain," *Br. J. Clin. Practice* 40(8): 326-330 (1986).

Holland & Gateley, "Drug therapy of mastalgia. What are the options?" *Drugs* 48(5): 709-716 (1994).

Irvin & Morrison, "Effectiveness of topical non-steroidal anti-inflammatory drugs in the management of breast pain," *J. R. Coll. Edinb.* 43(3):158-159 (1998).

Leonard, et al., "Randomized, double-blind, placebo-controlled, multicenter trial of 6% miltefosine solution, a topical chemotherapy in cutaneous metastases from breast cancer," *J. Clin. Oncol.* 19: 4150-4159 (2001).

Mansel & Dogliotti, "European multicentre trial of bromocriptine in cyclical mastalgia," *Lancet* 335(868): 190-193 (1990).

Mansel, et al., "A double blind trial of the prolactin inhibitor bromocriptine in painful benign breast disease," *Br. J. Surgery* 65(10): 724-27 (1978).

Mansel, et al., "Controlled trial of the antigonadotropin danazol in painful nodular benign breast disease," *Lancet* 1(8278): 928-933 (1982).

Millet & Dirbas, "Clinical management of breast pain: a review," *Obstet. Gynecol. Survey* 57(7): 451-461 (2002).

Nazli, et al., "Controlled trial of the prolactin inhibitor bromocriptine (Partodel) in the treatment of severe cyclical mastalgia," *Br J Clin Pract* 43:322-327 (1989).

Steinbrunn, et al., "Mastalgia. Tailoring treatment to type of breast pain," *Postgraduate Medicine* 102(5): 183-184; 187-187; 193-194 (1997).

Terwogt, et al., "Phase II trial of topically applied miltefosine solution in patients with skin-metastasized breast cancer," *Br. J. Cancer* 79:1158-1161(1999).

Unger, et al., "Hexadecylphosphocholine in the topical treatment of skin metastases in breast cancer patients," *Center Treat. Rev.* 17: 243-246 (1990).

Colacurci, et al., "Effects of tibolone on the breast", *Eur. J. Obstet. Gynecol. Reprod. Biol.*, 80(2):235-8 (1998).

Lufkin and Ory, "Relative value of transdermal and oral estrogen therapy in various clinical situations", *Mayo Clin. Proc.*, 69(2):131-5 (1994).

Moline, "Pharmacologic strategies for managing premenstrual syndrome", *Clin. Pharm.*, 12(3):181-96 (1993).

Plu-Bureau, et al., "Percutaneous progesterone use and risk of breast cancer: results from a French cohort study of premenopausal women with benign breast disease", *Cancer Detect. Prev.*, 23(4):290-6 (1999).

Fentiman, et al., "Tamoxifen and benign breast problems.", *Lancet*, 2(8567):1070-1072 (1987).

Montgomery, et al, "Treatment of severe cyclical mastalgia.", *J. R. Soc, Med.*, 72(7):489-491 (1979).

U.S. Appl. No. 12/497,865, filed Jul. 6, 2009, DiPiano, et al.

Akio, "Danazol Suppository", Patent Abstracts of Japan 15(263): (C-0847) (1991).

Anderson, et al., "Once daily controlled versus immediate release oxybutynin chloride for urge urinary incontinence. OROS Oxybutynin Study Group," *J. Urol.* 161: 1809-1812 (1999).

Barnhart, et al., "Distribution of a spermicide containing Nonoxynol-9 in the vaginal canal and the upper female reproductive tract", *Hum Reprod,.*16(6):1151-4 (2001).

Benita, et al., "Characterization of drug-loaded poly(d,l-lactide) microspheres," *J Pharm Sci* 73(12): 1721-1724 (1984).

Braun, et al., "Effect of danazol in vitro and in vivo on monocyte-mediated enhancement of endometrial cell proliferation in women with endometriosis," *Fertility and Sterility* 62(1): 89-95 (1994).

Brendler, et al., "Topical oxybutynin chloride for relaxation of dysfunctional bladders," *J. Urol.* 141(6): 1350-52 (1989).

Buyse, et al., "Intravesical oxybutynin for neurogenic bladder dysfunction: less systemic side effects due to reduced first pass metabolism," *J. Urol.* 160: 892-896 (1998).

Cicinelli, et al., "First uterine pass effect is observed when estradiol is placed in the upper buy not lower third of the vagina", *Fertility and Steriility*, 81(5):1414-1416 (2004).

Comer & Goa, "Extended-release oxybutynin," *Drugs Aging* 16: 149-155 (2000).

Das Neves, et al., "Gels as vaginal drug delivery systems", *Int. J. Pharm.* 2:318(1-2):1-14 (2006) Epub Mar 17. 2006.

De Ziegler, et al., "Administration non-orale de la progestérone: Expériences et avenir de la voie transvaginale," *Rev. Med. Suisse Romande* pp. 13-28 (1994) (with English abstract).

Farquhar, et al., "Management of dysfunctional uterine bleeding," Drugs 44(4): 378-384 (1992).

Femmepharma, "FP1096-001 Executive Summary," (2004).

Finnin and Morgan, "Transdermal penetration enhancers: applications, limitations, and potential", *J. Pharm. Sci.*, 88(10):955-8 (1999).

Geraghty, et al., "The in vitro release of some antimuscarinic drugs from monoolein/water lyotropic crystalline gels," *Pharm. Res.* 13(8): 1265-1271 (1996).

Goldenberg, "An extended-release formulation of oxybutynin chloride for the treatment of overactive urinary bladder," *Clin. Ther.* 21(4): 634-642 (1999).

Gupta & Sathyan, "Pharmacokinetics of an oral once-a-day controlled-release oxybutynin formulation compared with immediate-release oxybutynin," *J. Clin. Pharmacol.* 39: 289-296 (1999).

Guerriero, et al., "Influence of vaginal danazol on uterine and brain perfusion during hormonal replacement therapy", *Menopause*, 8(6); 424-428 (2001) (abstract only).

Hull, et al., "Endometriosis: An enigmatic disease," *J Women's Health* 5(2): 111-120 (1996).

Igarashi, "A new therapy for pelvic endometriosis and uterien adenomyosis: Local effect of vaginal and intrauterine danazol application," *Asia-Oceania J. Obstet. Gynaecol.* 16(1): 1-12 (1990).

Lim, et al., "Microencapsulation of living cells and tissues," *J Pharm. Sci.* 70(4): 351-354 (1981).

Liversidge, et al., "Particle size reduction for improvement of oral bioavailability of hydrophobic drugs: I. Absolute oral bioavailability of nanocrystalline danazol in beagle dogs", *Int J Pharm.*, 125:91-97 (1995).

Lobo, et al., "Vaginal route paradox: A direct transport to the uterus," *Symposium: The First Uterine Pass Effect*, Wyeth-Ayerst International, Inc. (1995).

Massad, et al., "The pharmacokinetics of intravesical and oral oxybutynin chloride," J. Urol. 148: 595-597 (1992).

Mathiowitz, et al., "Morphology of polyanhydride microsphere delivery system," *Scanning Microscopy* 4(2): 329-340 (1990).

Mathiowitz, et al., "Novel microcapsules for delivery systems," *Reactive Polymers* 6: 275-283 (1987).

Mathiowitz, et al., "Polyanhydride microsphperes as drug carriers I. Hot-melt microencapsulation," *J Controlled Release* 5:13-22 (1987).

Mathiowitz, et al., "Polyanhydride microspheres as drug carriers. II. Microencapsualtion by solvent removal," *J Appl. Polymer Sci.* 35: 755-774 (1988).

Mizutani, et al., "Danazol concentration in ovary, uterus, and serum and their effect on the hypothalamic-pituitary-ovarian axis during vaginal administration of a danazol suppository," *Feritility and Sterility* 63(6): 1184-1189 (1995).

*Physicians' Desk Reference*, Consult 1994 Supplements for Revisions, pp. 1372-1375.

Ramjee, et al., "Acceptability of Carraguard, a candidate microbicide and methyl cellulose placebo vaginal gels among HIV-positive women and men in Durban, South Africa", AIDS Res Ther. 4:20 pp. 1-10 (2007).

Saito, et al., "Treatment of overactive bladder with modified intravesical oxybutynin chloride," Neurol. Urodyn. 19: 683-688 (2000).

Salib, et al., "Utilization of sodium alginate in drug microencapsulation," Pharmazeutische Industrie 40(11A): 1230-1234 (1978).

Schröder, et al., "Absorption of oxybutinin from vaginal inserts: drug blood levels and the response of the rabbit bladder," Urology 56(6): 1063-1067 (2000).

Spooner, Classification of Side Effects to Danazol Therapy, Winthrop Laboratories, Surrey, England.

"Sultrin," *Physicians' Desk Reference*, 51$^{st}$ ed., pp. 1941 (1997).

Takebayashi, et al., "Danazol suspension injected into the uterine cervix of patients with adenomyosis and myoma. Preliminary study", *Gynecol. Obstet. Invest.*, 39(3):207-11 (1995) (abstract only).

"Terazol 7," *Physicians' Desk Reference*, 51$^{st}$ ed., pp. 1943 (1997).

The First Uterine Pass Effect—A new finding for new options in progesterone therapy, West-Ayerst Internation, Inc., pp. 1-2 (1995).

Thüroff, et al., "Randomized, double-blind, multicenter trial on treatment of frequency, urgency and incontinence related to detrusor hyperactivity: oxybutynin versus propantheline versus placebo," *J. Urol.* 145: 813-816 (1991).

Versi, et al., "Dry mouth with conventional and controlled-release oxybutynin in urinary incontinence," Obstet Gynecol. 95(5): 718-721 (2000).

Wagner, et al., "The novel progesterone receptor antagonists RTI 3021-012 and RTI 3021-022 exhibit complex glucocorticoid receptor antagonist activities: implications for the development of dissociated antiprogestins", Endocrinology, 140(3):1449-58 (1999).

Wellbery, et al., "Diagnosis and treatment of endometriosis", Am. Fam. Physician, 60:1753-68 (1999).

Wolthers Kluwer Health, Inc., "Summary Review: Oxybutynin Chloride 10 % Gel", Wolthers Kluwer Health, Inc., (2009).

Yamashita, et al., "Immunohistochemical determination of endometrial progesterone receptor (PR) content after intrauterine infusion of danazol in rabbits", Nippon Naibunpi Gakkai Zasshi, 69(10):1044-1050 (1993) (abstract only).

Zhang, et al., "Synthesis and progesterone receptor antagonist activities of 6-aryl benzimidazolones and benzothiazolones", Bioorg. Med. Chem. Lett., 11(20):2747-50 (2001).

\* cited by examiner

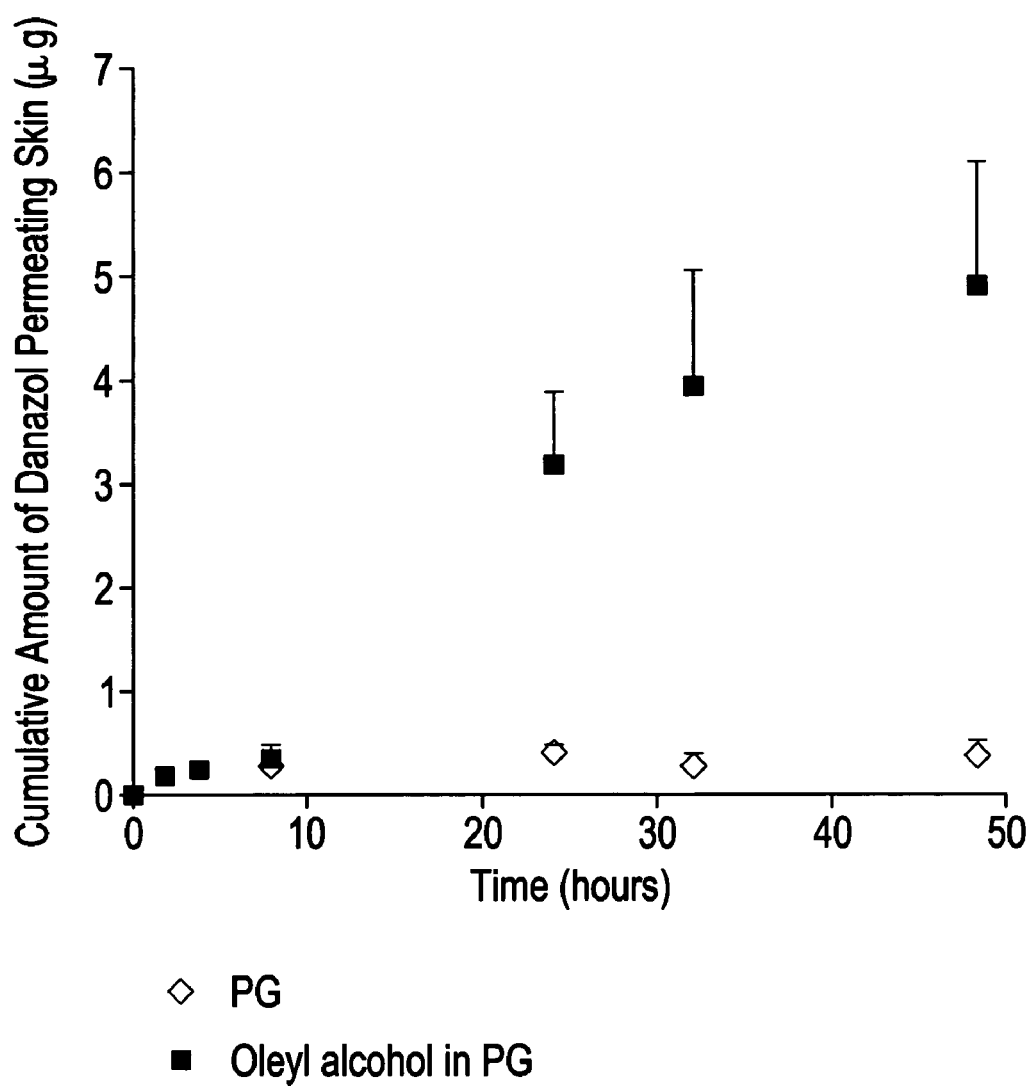

PHARMACEUTICAL PREPARATIONS FOR TREATMENTS OF DISEASES AND DISORDERS OF THE BREAST

CROSS-REFERENCE TO RELATED APPLICATIONS

This application claims priority to U.S. Ser. No. 60/437,778, entitled "Pharmaceutical Preparations for Treatments of Diseases and Disorders of the Breast", filed on Jan. 2, 2003 by Gerianne Tringali DiPiano and Peter Kevin Mays.

FIELD OF THE INVENTION

The present invention relates to pharmaceutical preparations for the treatment of diseases and disorders of the breast, chest and underlying musculature.

BACKGROUND OF THE INVENTION

Breast disorders are so common that B. Smith & W. Souba, *Breast disease*, p. 1, in *Breast Disease* 2, D. Wilmore, et al. (eds) (New York, Scientific America) (1995) estimate that one of every two women will consult her physician about a breast disorder at some point in her life. Clinically, the most useful classification system for benign breast disease is based on symptoms and physical findings. The six general categories of symptoms are:
1. Physiologic swelling and tenderness;
2. Nodularity, significant lumpiness, both cyclic and non-cyclic;
3. Mastalgia, severe pain, both cyclic and non-cyclic;
4. Dominant lumps, including gross lumps and fibroadenomas;
5. Nipple discharge, including intraductal papilloma and duct ectasia; and
6. Infections and inflammation, including subareolar, abscesses, lactational mastitis, breast abscesses and Mondor's Disease. See J. Isaacs, *Benign Neoplasms*, in D. Marchant, *Breast Disease*, p. 65-68 (W B Saunders, Philadelphia, Pa.) (1997).

Swelling, breast pain, and nodularity (Categories 1 and 2) are often grouped together and referred to as fibrocystic disease or changes. However, aggregating these categories may be problematic as the various causes of these symptoms may be isolated to determine the specific cause of the condition and the resultant treatment option to be undertaken. For example, women on oral contraceptives or hormone replacement therapy may experience swelling and breast tenderness (Category 1). By reducing or eliminating the estrogen replacement therapy, the breast pain or swelling may be reduced. Alternatively, breast pain may be caused by trauma, chest wall pain, or by costochondritis.

Dominant lumps (Category 4) are generally clinically benign breast lesions that are distinct, persistent, and relatively unchanging. The lesions that are represented by these lumps include macrocysts, galactoceles, and fibroadenomas. These lumps generally do not respond to hormonal therapy that may be effective in treating nodularity or breast pain.

Fibroadenomas (Category 4) represent the most common benign solid tumor of the female breast. They are typically seen in women in the third decade of life although they are sometimes seen in postmenopausal women. Fibroadenomas may respond to hormonal therapy and may change in size throughout the menstrual cycle.

Treatment options for breast disorders fall into two major categories, pharmacologic therapy and surgical approaches.

Before initiating any treatment, an assessment of dietary, hormone therapy and other factors must be taken into consideration. Women who use estrogen replacement therapy or oral contraceptives may discontinue therapy. In addition, dietary modification such as a reduction in saturated fat intake and caffeine consumption may reduce breast pain in certain women.

Drug treatment for breast pain is tailored to the severity of pain, chances of improvement with each drug, and potential adverse effects. P. Holland & C. Gately, *Drugs*, 48(5):709-716 (1994). Women with mild pain may be administered 6-8 capsules of gamma-linolenic acid (also known as "gamolenic acid" or "GLA") (40 mg) per day. The side effects associated with GLA are mild. For severe pain, the only approved treatment option is danazol, which is typically given in a dose of 100 mg to 200 mg per day. Danazol is highly effective, although it causes androgenic side effects which may reduce patient compliance. Controlled trials demonstrate that at oral doses of 200 mg to 400 mg per day, danazol produces a favorable clinical response in 70% to 80% of patients. C. Hinton, et al., *British J. Clinical Practice*, 40(8):326-30 (1986); R. Mansel, et al., *Lancet*, 8278: 928-933 (1982); and B. Steinbrum, et al., *Postgraduate Medicine*, 102(5):183-84, 187-87, and 193-94 (1997). In most instances, breast pain and tenderness are significantly relieved by the first month and eliminated in two to three months. Usually elimination of nodularity requires four to six months of therapy. However, high doses of danazol result in adverse side effects, which may include weight gain, voice change, development of facial and chest hair, loss of libido, acne, and central nervous system ("CNS") symptoms such as depression, anxiety, fatigue, nausea and diarrhea, as well as the inhibition of pregnancy while undergoing treatment. See e.g. Spooner, *Classification of Side Effects to Danazol Therapy*, Winthrop Laboratories, Surrey, England.

Bromocriptine, tamoxifen, and luteinizing hormone-releasing hormone (LHRH) analogues are not approved for the initial treatment of breast pain and fibrocystic breast disease, but are used to treat breast pain and fibrocystic disease that are resistant to other forms of treatment. The side effects associated with these drugs are severe.

Bromocriptine, which inhibits release of prolactin, is effective in up to 65% of women treated for cyclical mastalgia, i.e. breast pain which occurs in a regular pattern over time, at doses of 5mg per day. These results were confirmed in a multicenter, randomized, controlled study. K. Nazli et al., *Br J Clin Pract*, 43: 322-27 (1989); R. Mansel & L. Dogliotti, *Lancet*, 335 (868): 190-193 (1990). Improvement in symptoms was accompanied by a decrease in serum prolactin level. Mild side effects, including nausea, dizziness, headaches, and irritability have been reported in 30% of women, and 10% have complained of more severe side effects. These side effects can be minimized by altering the dosing regimen or reducing the amount of drug administered. However, R. Mansel et al., *BR J Surgery*, 65(10):724-27 (1978) noted that bromocriptine did not induce a response in patients with non-cyclical breast pain.

In severe cases of breast pain and fibrocystic breast disease, tamoxifen has been prescribed. Controlled trials demonstrated 80% to 90% success in treatment of cyclical mastalgia. I. Fentimen, et al., *Br. J. Clinical Prac. Sympt.*, 68:34-36 (1989). In addition, no difference in response was noted in women who received daily doses of 10 mg per day versus those who received daily doses of 20 mg per day. A decrease in side effects was noted however, in women who received 10 mg per day. I. Fentimen, et al., *BR J Surg.*, 75(9): 845-46 (1988).

Non-steroidal anti-inflammatory drugs (NSAIDs) are sometimes prescribed for the treatment of breast pain. A prospective study of the effectiveness of the topical application of NSAIDs as a gel formulation was carried out in 26 women with severe breast pain. A topical NSAID gel was applied as required and provided rapid relief of pain with no side effects in 81% of the women. A. Irving & S. Morrison, *JR Coll Edinb*, 43(3):158-9 (1998).

In non-cyclical mastalgia, and especially for chest wall pain, injections of lidocaine 1% (1 ml) and methylprednisone (40 mg) have been shown to be effective. Response rates of 90% have been reported, but about 50% of patients required a second injection 2 to 3 months later. A. Millet & F. Dirbas, *Obstetrical and Gynecological Survey*, 57(7): 459 (2002).

Miltefosine (also known as MILTEX® and hexadecylphosphocholine) has been used topically to treat cutaneous manifestations of metastatic breast cancer. See e.g. C. Unger et al., *Cancer Treat Rev* 17: 243-246 (1990); J. Terwogt et al., *Br J Cancer*, 79: 1158-1161 (1999); and R. Leonard et al., *J Clin Oncol*, 19: 4150-4159 (2001). These reports indicate that the cytostatic drug, miltefosine, is useful to treat topical lesions arising from a primary neoplasia event in the breast. However, the drug does not treat neoplastic lesions within the breast tissue and the cutaneous metastatic tissue need not be localized to breast skin. Therefore, the drug is merely acting topically at the site of administration. Further, the drug is not effective at treating the underlying disease of the breast.

Treatment of disorders and diseases of the breast and underlying musculature by traditional methods of oral or systemic administration is associated with a significant number of side effects and other complications that limit their use. For example, the normal digestive process may reduce bioavailability of drugs, requiring a higher dose be administered in order to achieve the desired effect. In addition, passage of the drug from the liver into the systemic circulation may convert the drug into a metabolite of the drug and cause a variety of untoward side effects. Either of these problems may cause patients to avoid their medications and disregard their doctors' treatment regimes.

It is therefore an object of the present invention to provide formulations and methods of administration to increase patient compliance and comfort during the treatment of diseases and disorders of the breast and chest.

It is a further object of the present invention increase the bioavailability of drug administered topically to the breast or chest as compared to drugs administered systemically.

BRIEF SUMMARY OF THE INVENTION

Formulations for topical or local administration of drugs other than non-steroidal antiinflammatories or analgesics such as lidocaine, such as hormones (and hormone releasing compounds) and analogs thereof, and chemotherapeutic agents, directly to the breast or chest to produce a regional or local effect with lower systemic drug levels than when an effective amount is administered systemically are disclosed herein. In a preferred embodiment, the drug is administered to the surface of the breast, areola, or directly to the nipple. The formulations provide increased patient comfort, increased bioavailability and relatively high blood levels in the region to be treated and have reduced side effects compared to when the same drugs are administered systemically. The preferred formulations contain drugs in the form of micro or nanoparticles, which may be formed of drug alone or in combination with an excipient or carrier. The excipient or carrier may modify the release rates or enhance absorption into the affected area. The drug formulation may be in the form of a cream, lotion or foam.

BRIEF DESCRIPTION OF THE DRAWING

FIG. 1 is a graph of time (hours) versus cumulative amount of danazol permeating through the breast skin (µg) for two different formulations, one containing propylene glycol as the carrier (◇) and the other containing propylene glycol and 5% oleyl alcohol as the carrier (■).

DETAILED DESCRIPTION OF THE INVENTION

The compositions and methods for administration thereof provide for significantly diminished side effects with increased bioavailability, as compared to systemic drug administration techniques.

As used herein, "locally" refers to delivery generally to the surface of the breast or chest and to the tissue immediately below the surface of the breast chest. As used herein, "regionally" refers to the general application site and its interrelated surrounding tissues. As used herein, "systemically" generally refers to the circulatory system and regions outside the spaces described above.

I. Formulations

The formulations are designed to provide maximum uptake in the affected tissues with rapid dissemination throughout the region to be treated, with little to no increase in systemic blood levels of the drug. In the preferred embodiment the active agent is in a micronized, nano-particle or micro-particle formulation. This may be achieved by milling the active agent or atomization of a solution containing the active agent, into a solvent extraction fluid, or other standard techniques for particle size reduction.

The formulation may include drug alone or in combination with excipients, carriers, and/or penetration enhancers. Excipients for topical administration may include: (a) antimicrobial compounds, e.g. parabens, (b) antioxidants, e.g. sodium ascorbyl acetate and alpha-tocopherol, (c) stabilizers, e.g. sorbitol, or (d) emulsifying agents to produce a stable emulsion with both a hydrophilic and a hydrophobic phase. In the preferred embodiment, the formulation is applied topically and is transdermally delivered to the tissue in need of treatment.

A. Active Agents

The term "drug" as generally used herein refers to any pharmacologically active substance capable of eliciting a desired alteration to a physiological system. The formulations may contain one or more active agents. Drugs may be synthetic or isolated natural compounds, proteins or peptides, antibodies, oligonucleotides or nucleotides, polysaccharides or sugars, or complexes of any of the above. Drugs may have a variety of activities, which may be inhibitory or stimulatory, including antibiotic, antiviral, antifungal, steroidal, cytotoxic, and anti-proliferative effects.

Other suitable active agents include media contrast agents and other diagnostic agents. Diagnostic agents may be delivered in the formulations to aid in disease diagnosis. A description of the various classes of suitable pharmacological agents and drugs may be found in Goodman and Gilman, *The Pharmacological Basis of Therapeutics*, (9th Ed., McGraw-Hill Publishing Co.) (1996).

In the preferred embodiment, the drug is a chemotherapeutic such as danazol, bromocriptine, or tamoxifen, or a hormone, hormone releasing agent, or analog thereof such as a LHRH analogue or an antiestrogen. In the most preferred embodiment, the active agent is danazol, an isoxazolo derivative of 17∝ ethenyltestosterone (an androgen hormone).

B. Excipients or Carriers

The drug is delivered to the breast tissue via local, topical or percutaneous delivery with suitable excipients or carriers to enable and/or enhance drug penetration. Suitable carriers or excipients may enhance the physical and chemical stability of the formulation or enhance its aesthetic properties.

The carrier may be any gel, ointment, lotion, emulsion, cream, foam, mousse, liquid, spray, or aerosol which is capable of delivering the drug to the breast tissue. In the local drug delivery vehicles described herein, a compounding agent, co-solvent, surfactant, emulsifier, antioxidant, preservative, stabilizer, or diluent may be included in the formulation. A suitable emulsifying agent is needed if the active agent is insoluble in an aqueous environment. A penetration enhancer may be added to enable the active agent to cross the barrier of the stratum corneum. In the preferred embodiment, the carrier is a gel, which is odorless and tasteless and dissolves rapidly, such as a hydroalcoholic gel.

Diluents may be included in the formulations to dissolve, disperse or otherwise incorporate the carrier. Examples of diluents include, but are not limited to, water, buffered aqueous solutions, organic hydrophilic diluents, such as monovalent alcohols, and low molecular weight glycols and polyols (e.g. propylene glycol, polypropylene glycol, glycerol, butylene glycol).

Appropriate excipients are selected based on the active agent and the type of the formulation. Standard excipients include gelatin, casein, lecithin, gum acacia, cholesterol, tragacanth, stearic acid, benzalkonium chloride, calcium stearate, glyceryl monostearate, cetostearyl alcohol, cetomacrogol emulsifying wax, sorbitan esters, polyoxyethylene alkyl ethers, polyoxyethylene castor oil derivatives, polyoxyethylene sorbitan fatty acid esters, polyethylene glycols, polyoxyethylene stearates, colloidal silicon dioxide, phosphates, sodium dodecyl sulfate, carboxymethylcellulose calcium, carboxymethylcellulose sodium, methylcellulose, hydroxyethylcellulose, hydroxypropylcellulose, hydroxypropylmethylcellulose phthalate, noncrystalline cellulose, magnesium aluminum silicate, triethanolamine, polyvinyl alcohol, polyvinylpyrrolidone, sugars, and starches.

C. Penetration Enhancers

Penetration enhancers are frequently used to promote transdermal delivery of drugs across the skin, in particular across the stratum corneum. Some penetration enhancers cause dermal irritation, dermal toxicity and dermal allergies. However, the more commonly used ones include urea, (carbonyldiamide), imidurea, N, N-diethylformamide, N-methyl-2-pyrrolidone, 1-dodecal-azacycloheptane-2-one, calcium thioglycate, 2-pyrrolidone, N,N-diethyl-m-toluamide, oleic acid and its ester derivatives, such as methyl, ethyl, propyl, isopropyl, butyl, vinyl and glycerylmonooleate, sorbitan esters, such as sorbitan monolaurate and sorbitan monooleate, other fatty acid esters such as isopropyl laurate, isopropyl myristate, isopropyl palmitate, diisopropyl adipate, propylene glycol monolaurate, propylene glycol monooleatea and non-ionic detergents such as Brij® 76 (stearyl poly(10 oxyethylene ether), Brij® 78 (stearyl poly (20)oxyethylene ether), Brij® 96 (oleyl poly(10)oxyethylene ether), and Brij® 721 (stearyl poly (21) oxyethylene ether) (ICI Americas Inc. Corp.).

D. Dosage

The compositions are administered to a patient in an amount that contains low dosages of drug. Typically the dosage in the topical formulation will be about one-tenth of the oral dosage. For danazol, the dosage range is from about 1 to 200 mg, preferably from about 10-50 mg/day.

II. Methods of Administration

The formulations are preferably administered topically to the surface of the breast or chest, transported transdermally and delivered to breast tissue. The compositions are administered to treat diseases and disorders of the breast, chest and the underlying musculature. In particular, the compositions may be administered to treat benign diseases of the breast, including mastalgia, mastodynia, Mondor's disease, fibrocystic breast disease, costochondritis, mastitis, Paget's disease of the areola, fibroadenoma, breast abscess, and breast infections. Typically these will be administered at least once a day or as needed.

The present invention will be further understood with reference to the following non-limiting examples.

Example 1

In Vitro Study of Skin Permeability with Danazol Formulations

Materials

Lucifer yellow was obtained from Molecular Probes (Eugene, Oreg.). Bovine serum albumin (BSA), oleyl alcohol and propylene glycol were obtained from Sigma-Aldrich (St. Louis, Mo.). Danazol was supplied by FemmePharma. The reservoir buffer contained filtered 1% BSA in Krebs Ringer bicarbonate (KRB) buffer, which contained 10 mM HEPES and 0.015 mM sodium bicarbonate at the pH of 7.4.

Tissue

Dermatomed human breast skin was obtained from Bioreclamation Inc. (Hicksville, N.Y.). The donor was a 72 year old, Caucasian female. The dermatomed skin consists only of epidermal layer and was kept frozen at −80° C. until the time of the study.

Formulations

Danazol solubility in propylene glycol was greater than 10 mg/mL. Two different carriers were tested. One carrier was propylene glycol and the second was 5% oleyl alcohol in propylene glycol. Oleyl alcohol is known to have skin permeation enhancing properties.

The first formulation ("Formulation 1") contained propylene glycol (10 mL), lucifer yellow (25.63 mg) and danazol (100.64 mg). The second formulation ("Formulation 2") contained propylene glycol (9.5 mL), oleyl alcohol (0.5 mL), lucifer yellow (25.46 mg) and danazol (100.61 mg). Lucifer yellow was included in the formulations to monitor membrane integrity during the experiment. Each formulation was run in four replicates from the one skin donor.

Permeation Study

The skin was thawed at room temperature for approximately 30 minutes and rinsed with saline. The skin was cut into approximately 3 cm$^2$ sections, which were clamped between the donor and receiver chambers of Franz diffusion cells. The receiver chamber was filled with 8 mL of reservoir buffer. A stirring bar mixed the reservoir contents. Then 0.2 mL of a formulation was placed directly on top of the skin in the donor chamber.

Each Franz diffusion cell was placed in a dry block heating/stirring module. The temperature was set at 40° C. in order to maintain 37° C. in the reservoir. The stirring rate was set at 10 (400 RPM). Samples (0.5 mL) were taken from the receiver chamber at 2, 4, 8, 24, 32, and 48 hours and replaced with an equal volume of reservoir buffer.

For the analysis of danazol, 200 µL of reservoir sample was diluted with 400 µL acetonitrile to precipitate the albumin, and centrifuged at 10,000 RPM for 10 minutes. At the end of the 48 hours incubation, samples were collected from the donor chamber for calculating the mass balance.

Sample Analyses

Lucifer yellow concentrations were measured using a FLUOstar fluorescence plate reader (BMG Laboratories, Durham, N.C.). The excitation and emission wavelengths were 485 and 538 nm, respectively. Danazol was measured by LC/MS using electrospray ionization.

Data Analysis

Cumulative concentrations in the receiver chamber were calculated compensating for the removal and replacement of the 0.5 mL sample, as follows.

$$C_r = C_n + (0.5\ mL/8.0\ mL) \times C_{n-1} \quad (Eq.\ 1)$$

where $C_n$ and $C_{n-1}$ are the measured receiver concentrations at time point n, and the previous time point, n−1, respectively.

The apparent permeability, $P_{app}$, was calculated as follows:

$$Flux = (dC_r/dt) \times V_r/A \quad (Eq.\ 2)$$

$$P_{app} = (dC_r/dt) \times V_r/(A \times C_0) \quad (Eq.\ 3)$$

where,
- $dC_r/dt$ is the slope cumulative concentration in the receiver chamber versus time in µg/mL
- $V_r$ is the volume of the receiver chamber (8 mL)
- A is the diffusional area of the exposed skin membrane (1.77 cm$^2$)
- $C_0$ is the initial concentration of compound in the formulation in µg/mL.

Danazol Permeation

The amounts of danazol that permeated into and/or through the skin at different times are plotted in FIG. 1. Skin permeability of danazol was clearly enhanced in the presence of 5% oleyl alcohol.

Flux and $P_{app}$ were estimated using the slope of the cumulative concentration vs. time profiles from 8 hours to 48 hours (see FIG. 1). Flux and $P_{app}$ values are presented in Table 1.

TABLE 1

Danazol Flux and $P_{app}$ Values

| | Danazol Flux (µg/cm$^2$/hr) | Danazol $P_{app}$ (10$^{-6}$, cm/hr) |
|---|---|---|
| Formulation 1 | 0.0034 ± 0.0015 | 0.32 ± 0.14 |
| Formulation 2 | 0.055 ± 0.016 | 4.83 ± 0.40 |

The donor chambers were sampled at the end of the 48 hour incubation period and assayed for danazol. These results are listed in Table 2. The propylene glycol carrier (Formulation 1) provided relatively low permeation as indicated by high percentages recovered in the donor compartment. This result is consistent with the results for permeation through the skin (see Table 1). However, Formulation 2, which used oleyl alcohol and propylene glycol as the carrier, delivered most of the danazol through the skin to the receiver chamber. This is indicated by the low percentages of danazol that remained in the donor chamber at 48 hours (see Table 2). Similarly, Table 1 demonstrates that a greater amount of danazol permeated into and/or through the skin with Formulation 2 than with Formulation 1. The permeability of danazol was approximately 13-fold greater using the carrier that contained 5% oleyl alcohol in propylene glycol, relative to the carrier that contained 100% propylene glycol.

TABLE 2

Danazol donor concentrations after the 48 hour incubation, and percentage remaining unabsorbed

| | Formulation 1 | | | | |
|---|---|---|---|---|---|
| | Skin 1 | Skin 2 | Skin 3 | Skin 4 | Average (1–3 only) |
| 0 hr | Not individually sampled | | | | 10.90 (mg/mL) |
| 48 hr | 12.00 (mg/mL) | 9.37 (mg/mL) | 8.73 (mg/mL) | 3.47 (mg/mL) | 10.03 (mg/mL) |
| Remaining % | 110.09 | 85.96 | 80.09 | 31.83 | 92.05 |

| | Formulation 2 | | | | |
|---|---|---|---|---|---|
| | Skin 5 | Skin 6 | Skin 7 | Skin 8 | Average |
| 0 hr | Not individually sampled | | | | 13.30 (mg/mL) |
| 48 hr | 1.43 (mg/mL) | 1.50 (mg/mL) | 1.14 (mg/mL) | 1.01 (mg/mL) | 1.27 (mg/mL) |
| Remaining % | 10.75 | 11.28 | 8.57 | 7.59 | 9.55 |

Lucifer Yellow Permeation

Each skin membrane was evaluated for permeation of lucifer yellow, which provides an indication of membrane integrity. There was no permeation of Lucifer yellow detectable until after 8 or 24 hours of incubation, indicating that these skin specimens were not permeable for this polar marker compound. Lucifer yellow $P_{app}$ values were similar for the values obtained for the carriers of Formulations 1 and 2 (see Table 1 for values).

Those skilled in the art will recognize, or be able to ascertain using no more than routine experimentation, many equivalents to the specific embodiments of the invention described herein. Such equivalents are intended to be encompassed by the following claims.

We claim:

1. A drug formulation comprising
   danazol in an amount providing regionally effective, not systemically effective, levels of danazol when administered transdermally to the breast, to provide relief from benign diseases or disorders of the breast,
   wherein the danazol is formulated in a hydroalcoholic gel comprising N-methyl-2-pyrrolidone or 2-pyrrolidone in an effective amount to solubilize danazol and to deliver danazol across the stratum corneum to the underlying breast tissue.

2. A method for treating a disease or disorder of the breast treatable with danazol comprising
   topically administering to the breast of a patient,
   a drug formulation comprising an effective amount of danazol in an amount providing regionally effective, not systemically effective, levels of danazol when administered transdermally to the breast tissue, to provide relief from benign diseases or disorders of the breast,
wherein the danazol is formulated in a hydroalcoholic gel comprising N-methyl-2-pyrrolidone or 2-pyrrolidone in an effective amount to solubilize danazol and to deliver danazol across the stratum corneum to the underlying breast tissue.

3. The method of claim 2 wherein the benign disease of the breast is selected from the group consisting of mastalgia, mastodynia, and fibrocystic breast disease.

4. The method of claim 2 wherein the region is the breast, areola, and underlying musculature of the chest.

* * * * *

UNITED STATES PATENT AND TRADEMARK OFFICE
CERTIFICATE OF CORRECTION

PATENT NO. : 7,812,010 B2  
APPLICATION NO. : 10/751056  
DATED : October 12, 2010  
INVENTOR(S) : Gerianne Tringali DiPiano, Peter Kevin Mays and John Ziemniak It is certified that error appears in the above-identified patent and that said Letters Patent is hereby corrected as shown below:

Title page, item (73) replace "Femmepharma, Inc." with --FemmePharma Holding Co., Inc.--.

Signed and Sealed this
Fifth Day of April, 2011

David J. Kappos
*Director of the United States Patent and Trademark Office*